United States Patent
Wiggins et al.

(10) Patent No.: US 11,038,528 B1
(45) Date of Patent: Jun. 15, 2021

(54) GENETIC PROGRAMMING BASED COMPRESSION DETERMINATION

(71) Applicant: International Business Machines Corporation, Armonk, NY (US)

(72) Inventors: Paul S. Wiggins, Kingston, NY (US); Don Eric Kallberg, Bethel, CT (US); Steven Sullivan, South Glens Falls, NY (US); Marc Henri Coq, Hopewell Junction, NY (US); Luis manon, Poughkeepsie, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

(21) Appl. No.: 16/892,418

(22) Filed: Jun. 4, 2020

(51) Int. Cl.
*H03M 7/30* (2006.01)
*G06F 16/23* (2019.01)
*G16B 50/50* (2019.01)

(52) U.S. Cl.
CPC ...... *H03M 7/6082* (2013.01); *G06F 16/2379* (2019.01); *G16B 50/50* (2019.02); *H03M 7/70* (2013.01)

(58) Field of Classification Search
CPC ...... H03M 7/6082; H03M 7/70; G16B 50/50; G06F 16/2379
USPC ...................................................... 341/87, 51
See application file for complete search history.

(56) References Cited

U.S. PATENT DOCUMENTS

| | | | |
|---|---|---|---|
| 6,327,582 B1 | 12/2001 | Worzel | |
| 6,885,319 B2* | 4/2005 | Geiger | H03M 7/30 341/51 |
| 7,609,179 B2 | 10/2009 | Diaz-Gutierrez et al. | |
| 9,385,749 B1* | 7/2016 | Nam | H03M 7/607 |
| 9,753,696 B2 | 9/2017 | Livshits et al. | |
| 2002/0078431 A1 | 6/2002 | Reps | |
| 2002/0169563 A1 | 11/2002 | Carvalho Ferreira | |

(Continued)

FOREIGN PATENT DOCUMENTS

| | | | |
|---|---|---|---|
| WO | 2006096162 | * | 9/2006 |
| WO | 2006096162 A2 | | 9/2006 |

(Continued)

OTHER PUBLICATIONS

Aysha, "Document Image Segmentation and Compression using Artificial Neural Networks and Evolutionary Methods." Cochin University of Science and Technology Diss, (2013). 160 Pages.

(Continued)

*Primary Examiner* — Khai M Nguyen
(74) *Attorney, Agent, or Firm* — Cantor Colburn LLP; Teddi Maranzano

(57) ABSTRACT

Techniques for genetic programming based compression determination are described herein. An aspect includes adding a first plurality of randomly generated compression algorithms to a first set of compression algorithms. Another aspect includes determining a respective mutated version of each of the first plurality of randomly generated compression algorithms. Another aspect includes adding the determined mutated versions to the first set of compression algorithms. Another aspect includes evaluating and ranking the first set of compression algorithms based on respective achieved degrees of compression.

20 Claims, 5 Drawing Sheets

(56) References Cited

U.S. PATENT DOCUMENTS

2014/0195497 A1    7/2014   Amit et al.
2019/0303719 A1    10/2019   Hamilton et al.

FOREIGN PATENT DOCUMENTS

WO    2019191153    * 10/2019
WO    2019191153 A1    10/2019

OTHER PUBLICATIONS

Banks et al. "A comparison of selection, recombination, and mutation parameter importance over a set of fifteen optimization tasks." Proceedings of the 11th Annual Conference Companion on Genetic and Evolutionary Computation Conference: Late Breaking Papers. ACM, 2009. 6 Pages.
Koza, "Genetically breeding populations of computer programs to solve problems in artificial intelligence." [1990] Proceedings of the 2nd International IEEE Conference on Tools for Artificial Intelligence. IEEE, 1990. 9 Pages.
Miller, "Cartesian genetic programming." Cartesian Genetic Programming. Springer, Berlin, Heidelberg, 2011. pp. 17-34.
Piszcz et al., "A survey of mutation techniques in genetic programming." Proceedings of the 8th annual conference on Genetic and evolutionary computation. ACM, 2006. 2 pages.
Willis et al. "Genetic programming: An introduction and survey of applications." Second international conference on genetic algorithms in engineering systems: innovations and applications. IET, 1997. 8 Pages.

* cited by examiner

GENETIC PROGRAMMING BASED COMPRESSION DETERMINATION

BACKGROUND

The present invention generally relates to computer systems, and more specifically, to genetic programming based compression determination for use in conjunction with a computer system.

Data compression is a process that encodes information in an original file so that the information in the original file can be expressed with fewer bits. Compression is implemented to reduce the consumption of expensive resources, for example, hard disk space while storing information, transmission bandwidth while transmitting information, etc. Due to the demand for reduction of the consumption of resources, compression techniques have been developed quickly, and many compression algorithms have been proposed. Different compression formats are utilized in different compression algorithms, such as ZIP, RAR format in Microsoft® Windows® operating system, and gz and bz format for Linux®/Unix® operating system.

SUMMARY

Embodiments of the present invention are directed to genetic programming based compression determination. A non-limiting example computer-implemented method includes adding a first plurality of randomly generated compression algorithms to a first set of compression algorithms. The method also includes determining a respective mutated version of each of the first plurality of randomly generated compression algorithms. The method also includes adding the determined mutated versions to the first set of compression algorithms. The method also includes evaluating and ranking the first set of compression algorithms based on respective achieved degrees of compression.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

DETAILED DESCRIPTION

Figure 1:
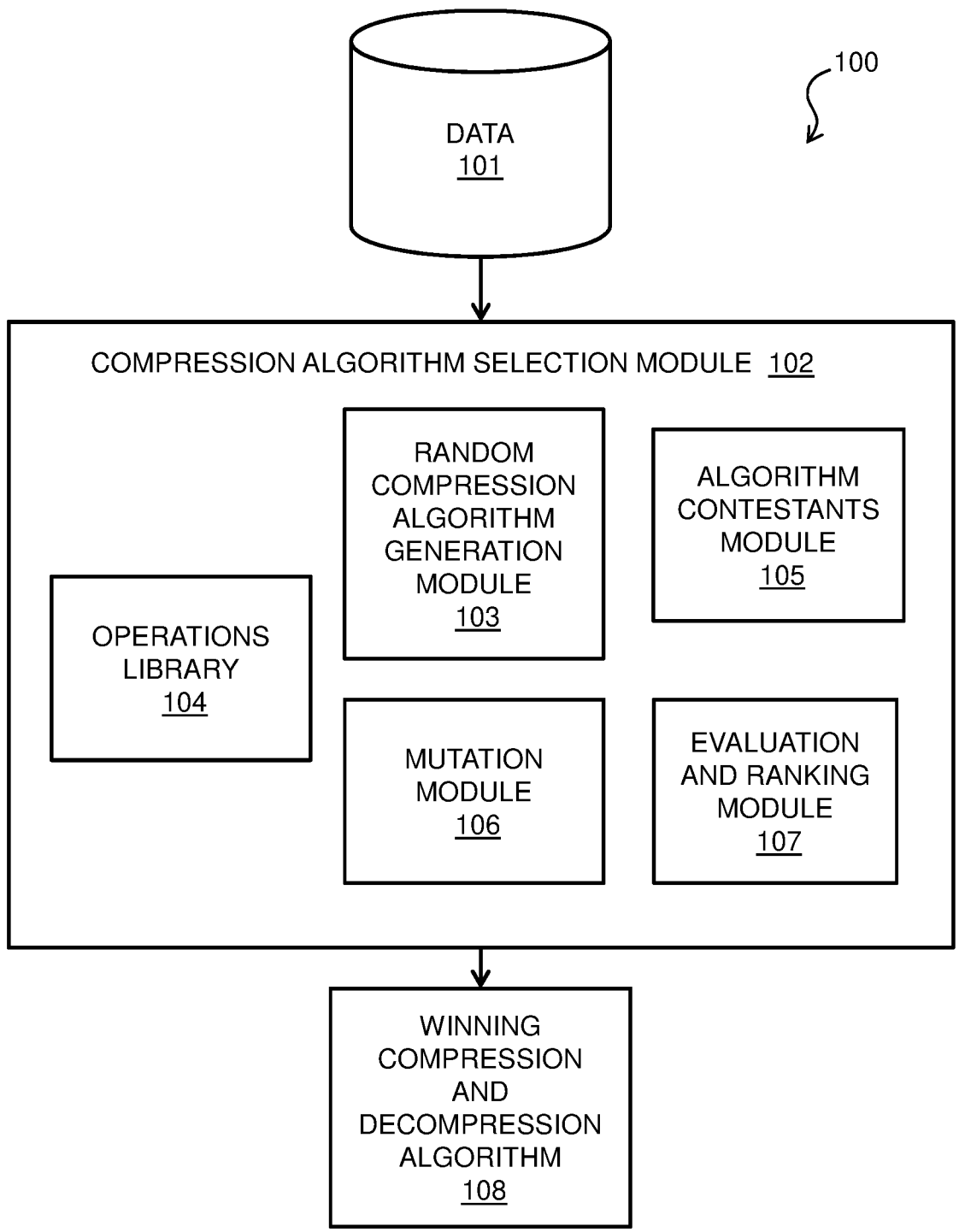
FIG. 1 is a block diagram of components of a system for genetic programming based compression determination in accordance with one or more embodiments of the present invention.

One or more embodiments of the present invention provide genetic programming based compression determination. In a computing environment, there may be large quantities of data that need to be transferred and/or stored. The transmission and storage of relatively large quantities of data may require extensive storage and transmission resources, and take a long time. Enhancement of data compression can preserve storage and bandwidth resources. A number of compression algorithms and associated decompression algorithms can be developed for respective particular data types using iterative genetic programming techniques. A set of compression algorithms can be randomly generated and iteratively tested for the data type in order to select a winning compression algorithm to be associated with a data type. Mutated versions of the randomly generated compression algorithms can also be generated and evaluated.

The data corresponding to the data type can be represented in a matrix format. A compression algorithm can receive data represented as a matrix of numbers, and perform any appropriate number of reversible matrix operations on the matrix of numbers to generate a smaller matrix of numbers. An associated decompression algorithm can receive the smaller matrix of numbers, and reverse the matrix operations included in the compression algorithm to regenerate the original matrix of numbers. Compression algorithms can be randomly generated based on a library of reversible matrix operations. In some embodiments of the invention, an initial set of randomly generated algorithms can be evaluated and ranked according to a respective degree of compression achieved by each of the algorithms for the particular data type. A subset of the algorithms comprising a top tier (e.g., about 25%) of the initial set of randomly generated algorithms can be selected for further evaluation, and the lower tier compression algorithms (e.g., the bottom 75%) can be discarded. A second set of compression algorithms can be generated including the selected top tier algorithms, a mutated set of algorithms corresponding to the selected top tier algorithms, and an additional set of randomly generated algorithms. In some embodiments of the invention, the mutated algorithms can be generated by substituting one or more the operations in each top tier algorithm with a different operation from the library of reversible matrix operations. The compression algorithms in the second set can be evaluated and ranked based on the degree of compression achieved for the data type, and a third set can be generated based on the ranking. Additional sets of algorithms can be generated and evaluated until a stop condition (e.g., an amount of processing time, or a plateauing of the degree of achieved compression) is met. The winning compression and associated decompression algorithm can be assigned to be used for data transmission and/or storage for the particular data type.

A compression application can include any appropriate number of compression algorithms that were determined based on genetic programming techniques, each compression algorithm being associated with a particular data type.

In some embodiments of the invention, the compression application can divide an input data file into a series of matrices and process each matrix using the compression algorithm chosen by the algorithm identifier, and append the output matrices into a compressed output file. A decompression application can include an associated respective decompression algorithm for each of the compression algorithms in the compression application. In some embodiments of the invention, the compression application can output compressed files having a particular file extension (e.g., *.ucf, for "ultra-compressed file"), and include a data type identifier and/or a compression algorithm identifier in the metadata of the compressed file. The decompression application can select the appropriate decompression algorithm to apply to a compressed file based on the algorithm identifier in the file metadata, and output a decompressed file having a file type corresponding to the data type identifier in the file metadata. In some embodiments of the invention, multiple versions of a compression/decompression algorithm may be maintained for a particular file type; in such embodiments, the compressed file metadata can include a version number.

Turning now to FIG. 1, system 100 for genetic programming based compression determination is generally shown in accordance with one or more embodiments of the present invention. System 100 can be implemented in conjunction with any appropriate computer device, such as computer device 500 of FIG. 5. System 100 includes data 101 and compression algorithm selection module 102. Data 101 can include any appropriate amount and type(s) of data (e.g., video data, audio data, image data, telemetry data, account data, medical data, user data, and/or sensor data). Compression algorithm selection module 102 includes random compression algorithm generation module 103, operations library 104, algorithm contestants module 105, mutation module 106, and evaluation and ranking module 107. Random compression algorithm generation module 103 randomly generates compression algorithms based on operations library 104. Operations library 104 can include a set of reversible mathematical matrix operations; any appropriate reversible matrix operations may be included in operations library 104. Each generated compression algorithm from random compression algorithm generation module 103 can include any appropriate number of operations selected from operations library 104 arranged in any appropriate sequence. Algorithm contestants module 105 receives randomly generated compression algorithms from random compression algorithm generation module 103, and iteratively determines winning compression and decompression algorithm 108 based on input from evaluation and ranking module 107 and mutation module 106. Operation of system 100 is discussed below in further detail with respect to FIGS. 2 and 3, and implementation of the winning compression and decompression algorithm 108 is discussed below in further detail with respect to FIG. 4.

It is to be understood that the block diagram of FIG. 1 is not intended to indicate that the system 100 is to include all of the components shown in FIG. 1. Rather, the system 100 can include any appropriate fewer or additional components not illustrated in FIG. 1 (e.g., additional memory components, embedded controllers, functional blocks, connections between functional blocks, modules, inputs, outputs, etc.). Further, the embodiments described herein with respect to system 100 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

Figure 2:
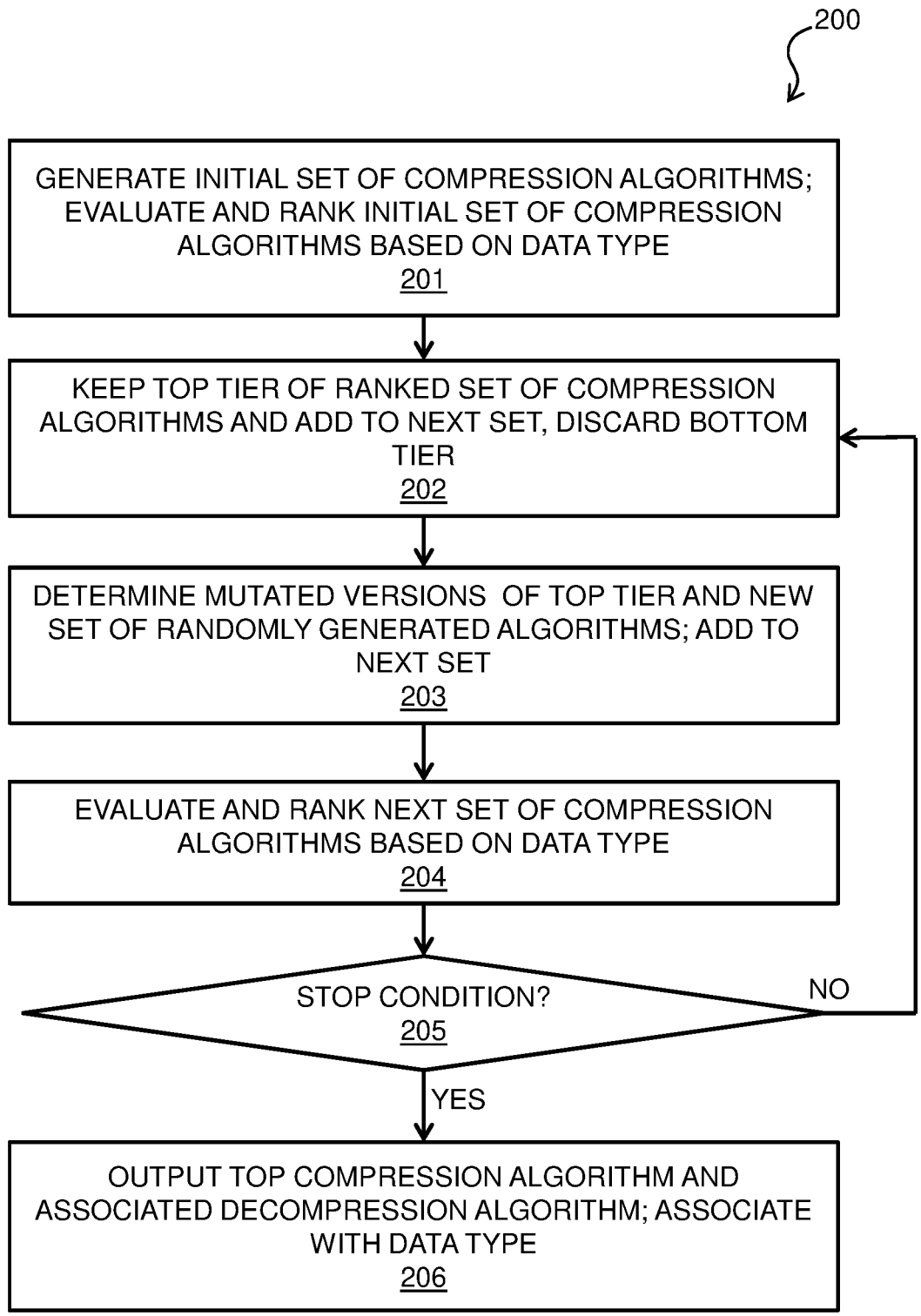
FIG. 2 is a flow diagram of a process for genetic programming based compression determination in accordance with one or more embodiments of the present invention.

FIG. 2 shows a process flow diagram of a method 200 for genetic programming based compression determination in accordance with one or more embodiments of the present invention. Method 200 can be implemented in conjunction with any appropriate computer device, such as computer device 500 of FIG. 5. Method 200 can be implemented in embodiments of, and is discussed in reference to, system 100 of FIG. 1. In block 201 of method 200, an initial set of compression algorithms is randomly generated by random compression algorithm generation module 103 and provided to algorithm contestants module 105, and then evaluated and ranked by evaluation and ranking module 107 based on first input data from data 101. The first input data may be of any appropriate data type or, in some embodiments of the invention, of an unknown data type, and may include a single file or a group of files in various embodiments. The first input data of block 201 may not include compressed data in some embodiments of the invention (e.g., data that has already been compressed by a compression application such as compression application 401 of FIG. 4, for example, any file having a *.ucf file extension). The initial set of randomly generated compression algorithms from random compression algorithm generation module 103 can include sequences of randomly chosen operation codes from operations library 104. Each operation code can correspond to a distinct reversible mathematical operation that can be performed on a numerical matrix. The sequence of operation codes in each of the randomly generated compression algorithms can be any appropriate length. Evaluation and ranking module 107 determines a degree of compression achieved by each compression algorithm in the initial set for the first input data from data 101. Each of the initial set of compression algorithms processes the same input data, such that the compression algorithms can be compared and ranked according to compression performance as determined by evaluation and ranking module 107. In some embodiments, the first input data may be divided up into numerical matrices that are provided to each of the initial set of compression algorithms. After each compression algorithm of the initial set of compression algorithms is done processing the entirety of the first input data, each respective compressed output data is measured to determine a degree of compression achieved by the corresponding compression algorithm. The compression algorithms in the initial set of compression algorithms are ranked based on the respective measured degrees of compression in block 201.

In block 202, a top tier of the ranked initial set of compression algorithms are kept in algorithm contestants module 105, and the remaining bottom tier are discarded by algorithm contestants module 105. Any appropriate percentage of the ranked initial set of compression algorithms may be kept by algorithm contestants module 105; in some embodiments of block 202, the top 25% of the compression algorithms are kept, and the bottom 75% are discarded. The top tier of the compression algorithms from the initial set are added to a next set of compression algorithms in algorithm contestants module 105.

In block 203, mutated versions of the top tier of compression algorithms, as determined by mutation module 106, and a new set of randomly generated compression algorithms from random compression algorithm generation module 103 are added to the next set of compression algorithms. In some embodiments, the mutations can include substituting at least one randomly chosen operation code in each of the top tier algorithms with another randomly-chosen operation code from operations library 104 by mutation module 106.

In block 204, the degree of compression achieved by each of the next set of compression algorithms is evaluated by evaluation and ranking module 107 using second input data from data 101, and the next set of compression algorithms is ranked based on the determined degrees of compression. The second input data and the first input data are of the same data type. In block 205, it is determined whether a stop condition has occurred. The stop condition can include an amount of processing time having elapsed, or the degree of compression that is achieved by the top ranked compression algorithm in the ranked set of compression algorithms being determined to have plateaued (e.g., has not significantly increased) across a number of iterations of blocks 202-205 in various embodiments of the invention. If it is determined in block 205 that the stop condition has not occurred, flow proceeds back to block 202 from block 205, and the top tier of the ranked set of compression algorithms is kept and added to a next set of compression algorithms, and the bottom tier is discarded. The next set of compression algorithms is constructed according to block 203, and evaluated and ranked according to block 204 based on next input data from data 101 having a same data type as the first and second input data. Blocks 202, 203, and 204 can be repeated any appropriate number of times to generate, evaluate, and rank any appropriate number of sets of compression algorithms until it is determined that the stop condition has occurred in block 205. In some embodiments of method 200, the percentage of the ranked set of compression algorithms that is included in the top tier that is kept in block 202 may be adjusted in subsequent iterations of blocks 202, 203, and 204. In some embodiments of method 200, for each repetition of blocks 202, 203, and 204, different input data, comprising a single file or a group of files, from data 101 corresponding to the data type can be selected and used for evaluation and ranking of the set of compression algorithms in block 204.

If it is determined in block 205 that the stop condition has occurred, flow proceeds to block 206, in which the top compression algorithm and corresponding decompression algorithm from the current ranked set of compression algorithms (i.e., as determined by the most recent iteration of block 204) is output as winning compression and decompression algorithm 108. The corresponding decompression algorithm performs the operations of the winning compression algorithm in reverse order to reconstruct compressed data from the winning compression algorithm. The winning compression and decompression algorithm 108 are assigned to the particular data type of the input data that was used to determine winning compression and decompression algorithm 108, and may be assigned an algorithm identifier and a version number corresponding to the data type in some embodiments.

The process flow diagram of FIG. 2 is not intended to indicate that the operations of the method 200 are to be executed in any particular order, or that all of the operations of the method 200 are to be included in every case. Additionally, the method 200 can include any suitable number of additional operations.

Figure 3:
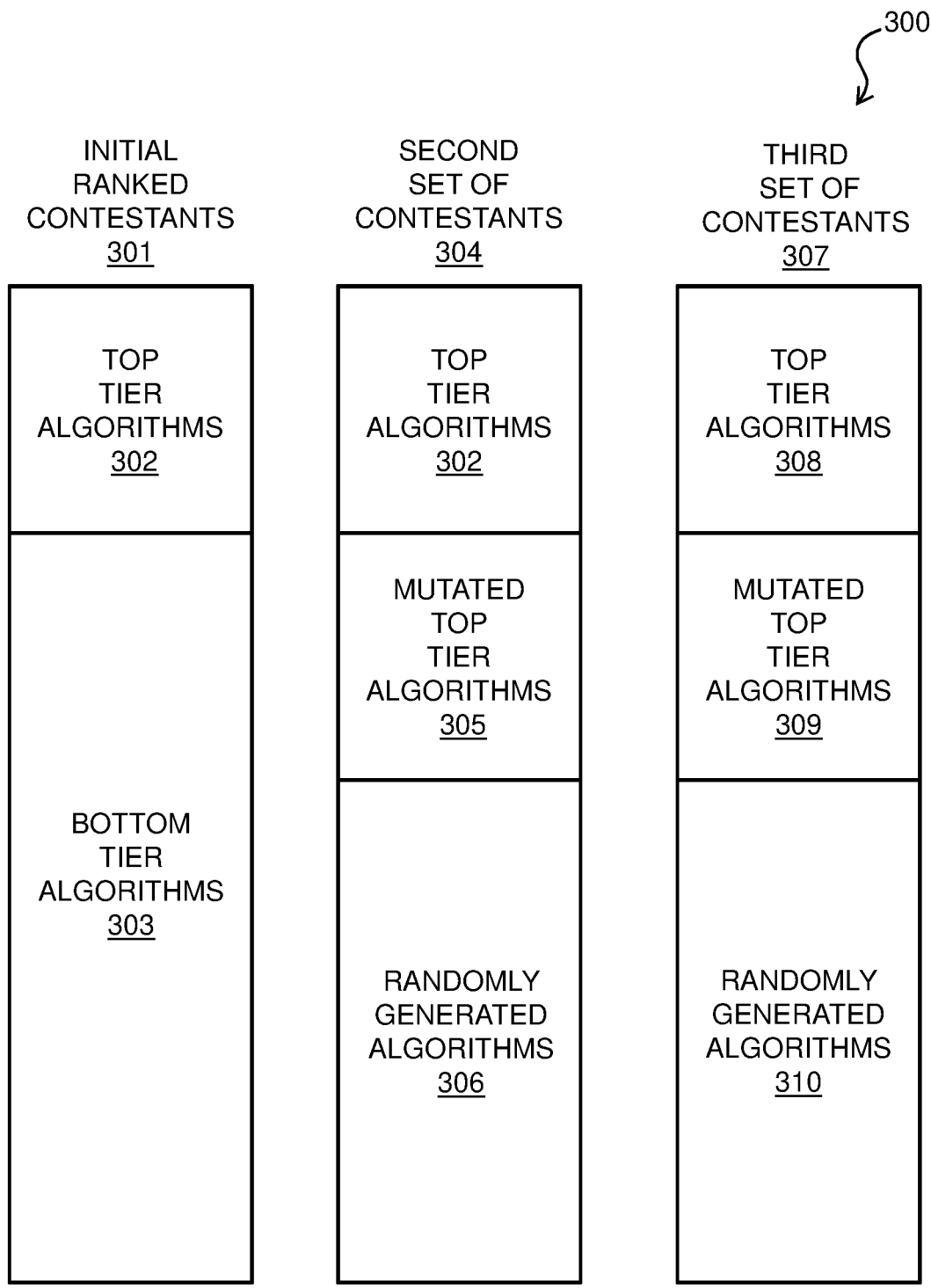
FIG. 3 is a block diagram of components of a system for genetic programming based compression determination in accordance with one or more embodiments of the present invention.

FIG. 3 shows a system 300 for genetic programming based compression determination in accordance with one or more embodiments of the present invention. System 300 can be implemented in conjunction with any appropriate computer device, such as computer device 500 of FIG. 5, and can be implemented in embodiments of algorithm contestants module 105 of system 100 of FIG. 1. System 300 includes an initial set of ranked contestants 301 comprising a number of randomly generated compression algorithms (i.e., generated by random compression algorithm generation module 103 of FIG. 1, and evaluated and ranked by evaluation and ranking module 107 according to block 201 of method 200 of FIG. 2). As described above with respect to block 202 of method 200 of FIG. 2, the initial set of ranked contestants 301 is separated into top tier algorithms 302 and bottom tier algorithms 303. Top tier algorithms 302 are included in second set of contestants 304, and bottom tier algorithms 303 are discarded. Any appropriate percentages may be used to determine top tier algorithms 302 and bottom tier algorithms 303; in some embodiments of the invention, top tier algorithms 302 may be about 25% of the initial ranked contestants 301, and bottom tier algorithms 303 may be about 75% of the initial ranked contestants 301.

Second set of contestants 304 also includes mutated top tier algorithms 305 and randomly generated algorithms 306, as described above with respect to method 203 of method 200 of FIG. 2. Each of top tier algorithms 302 may correspond to a single respective mutated algorithm in mutated top tier algorithms 305. In some embodiments, mutated top tier algorithms 305 can be generated by substituting at least one randomly chosen operation code in each of the top tier algorithms 302 with another randomly-chosen operation code from operations library 104 by mutation module 106. Randomly generated algorithms 306 may include new randomly generated compression algorithms that are generated by random compression algorithm generation module 103 of FIG. 1. In some embodiments of the invention, top tier algorithms 302 may be about 25% of second set of contestants 304, mutated top tier algorithms 305 may be about 25% of the second set of contestants 304, and randomly generated algorithms 306 may be about 50% of second set of contestants 304.

The second set of contestants 304 is evaluated and ranked by evaluation and ranking module 107 according to block 204 of method 200, and top tier algorithms 308 are determined based on the ranked second set of contestants. Top tier algorithms 308 may include compression algorithms from any of top tier algorithms 302, mutated top tier algorithms 305, and/or randomly generated algorithms 306. Top tier algorithms 308 are added to third set of contestants 307 as described with respect to block 202 of method 200 of FIG. 2. Third set of contestants 307 also includes mutated top tier algorithms 309, which correspond to top tier algorithms 308, and randomly generated algorithms 310, which may include new randomly generated compression algorithms that are generated by random compression algorithm generation module 103 of FIG. 1, as described with respect to block 203 of method FIG. 2. In some embodiments of the invention, top tier algorithms 308 may be about 25% of third set of contestants 307, mutated top tier algorithms 309 may be about 25% of the third set of contestants 307, and randomly generated algorithms 310 may be about 50% of third set of contestants 307. Any appropriate number of sets of contestants generated according to method 200 of FIG. 2 may be included in embodiments of system 300 of FIG. 3.

It is to be understood that the block diagram of FIG. 3 is not intended to indicate that the system 300 is to include all of the components shown in FIG. 3. Rather, the system 300 can include any appropriate fewer or additional components not illustrated in FIG. 3 (e.g., compression algorithms, sets of contestants, additional memory components, embedded controllers, functional blocks, connections between functional blocks, modules, inputs, outputs, etc.). Further, the embodiments described herein with respect to system 300 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

Figure 4:
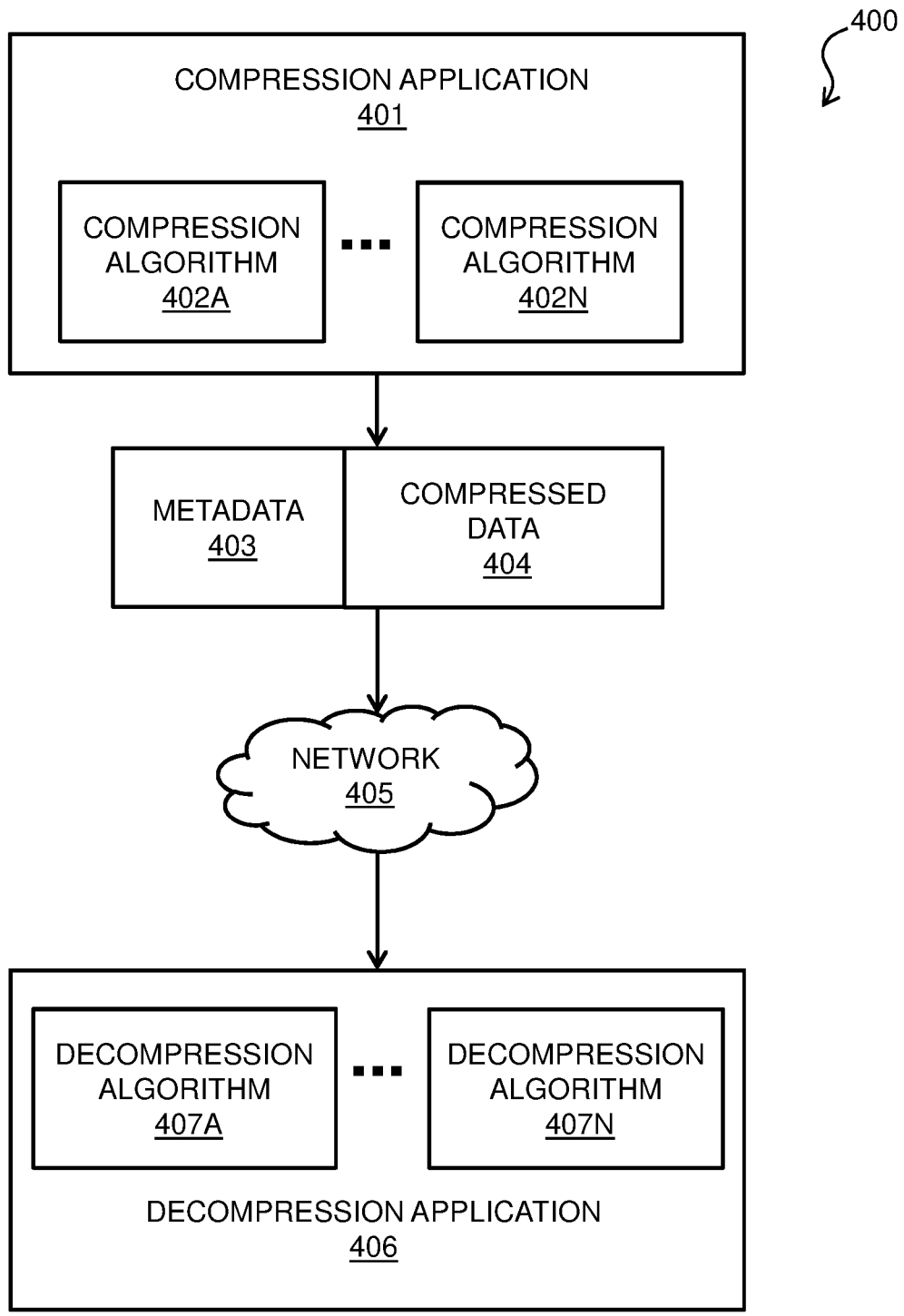
FIG. 4 is a block diagram of components of a system including genetic programming based compression determination in accordance with one or more embodiments of the present invention.
Figure 5:
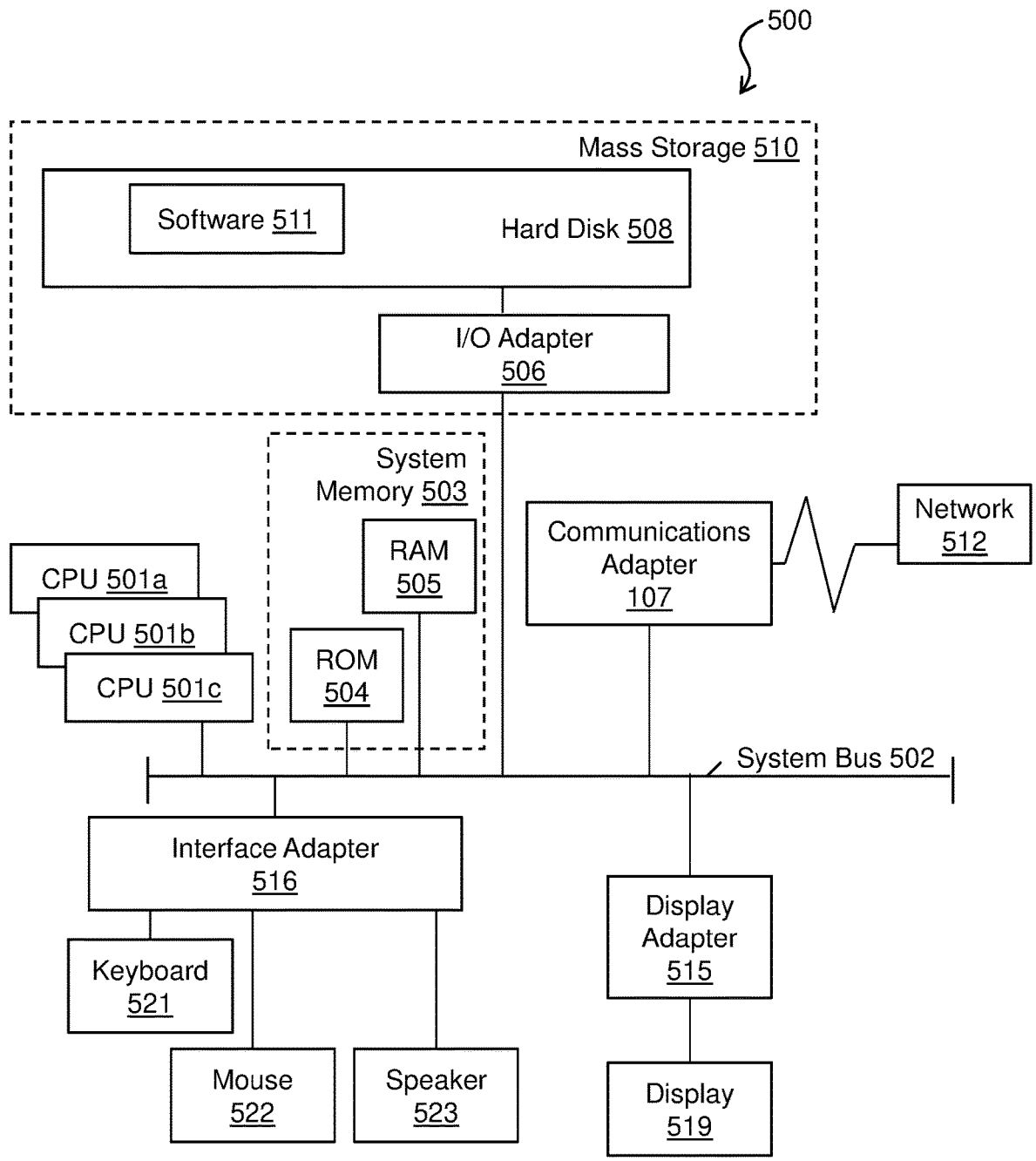
FIG. 5 is a block diagram of an example computer system for use in conjunction with one or more embodiments of genetic programming based compression determination.

FIG. 4 shows a system 400 including genetic programming based compression determination in accordance with one or more embodiments of the present invention. System 400 can be implemented in conjunction with embodiments of winning compression and decompression algorithm 108 of system 100 of FIG. 1. As shown in FIG. 5, system 500 includes a compression application 401 that is in communication with decompression application 406 via network 405. Each of compression application 401 and decompression application 406 may be running on any appropriate computer device, such as computer device 500 of FIG. 5. Network 405 may include any appropriate digital communications medium. In some embodiments of the invention according to system 400, compression application 401 and decompression application 406 may run on the same computer device. In some embodiments of the invention according to system 400, a computer device that is running both compression application 401 and decompression application 406 may be in communication via network 405 with another computer device that is running another instance of both compression application 401 and decompression application 406. Compression application 401 includes a plurality of compression algorithms 402A-N, and decompression application 406 includes a plurality of decompression algorithms 407A-N. Each compression algorithm 402A-N corresponds to a single respective decompression algorithm 407A-N, and each compression/decompression algorithm pair corresponds a winning compression and decompression algorithm 108 that were generated for a respective data type by system 100 according to method 200 of FIG. 2.

Each compression/decompression algorithm pair corresponds to a respective data type. Compression application 401 may receive data files as input, and assign each received data file to a respective compression algorithm of compression algorithms 402A-N based on a data type of the data file. In some embodiments of the invention, the data files received as input by compression application 401 may include data that has not already been compressed by a compression application such as compression application 401 (e.g., compression application 401 may not be used to compress the same data multiple times). The data types recognized by the compression application 401 may include any appropriate data types, and in some embodiments may be determined based on a file type of a data file and/or a source of a data file. For example, data of a particular file type belonging to a particular subgroup of an organization that is using compression application 401 may have an assigned compression algorithm in compression application 401 that is distinct from the compression algorithm for data of the particular file type belonging to a different subgroup of the organization. In some embodiments, compression application 401 may examine a file extension, a file name, and/or metadata of an incoming uncompressed data file in order to determine the appropriate compression algorithm of compression algorithms 402A-N for the uncompressed data file. In some embodiments of the present invention, the data types recognized by compression application 401 may not include compressed data (e.g., any files having a *.ucf file extension).

In some embodiments of the invention, the compressed data files output by any of the compression algorithms 402A-N in compression application 401 may have the same file extension (e.g., *.ucf). A compressed file that is output by compression algorithm 402N of compression application 401 includes metadata 403 and compressed data 404. Metadata 403 can include a file type of the uncompressed data file, and an algorithm identifier of the compression algorithm 402N that generated the compressed data 404. Compressed data 404 can include the reduced numerical matrix data that was generated by the compression algorithm 402N. In some embodiments, the algorithm identifier can include a version number. The compressed data is received by decompression application 406. Decompression application 406 may examine the metadata 403 to determine the algorithm identifier, and provide the compressed data 404 to decompression algorithm 407N based on the determined algorithm identifier. Decompression algorithm 407N may reverse the operations of the associated compression algorithm 402N to reconstruct the uncompressed data corresponding to compressed data 404. The uncompressed data may be assigned a file type by decompression application 406 based on metadata 403.

Files that are compressed by compression application 401 can be stored onto a dedicated storage device for backup files. For example, a central server can be used by a business to store data that is compressed by compression application 401 in a compacted form to save on disk space, and the uncompressed data can be provided from the central server to users via decompression application 406. In another example, data can be compressed at an originating location by compression application 401, the compressed data can be sent over a remote network 405 to another site, and the received data can be stored in compressed form at the another site and/or decompressed by decompression application 406.

It is to be understood that the block diagram of FIG. 4 is not intended to indicate that the system 400 is to include all of the components shown in FIG. 4. Rather, the system 400 can include any appropriate fewer or additional components not illustrated in FIG. 4 (e.g., additional input data, computer systems, networks, applications, compression algorithms, decompression algorithms, memory components, embedded controllers, functional blocks, connections between functional blocks, modules, inputs, outputs, etc.). Further, the embodiments described herein with respect to system 400 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

Turning now to FIG. 5, a computer system 500 is generally shown in accordance with an embodiment. The computer system 500 can be an electronic, computer framework comprising and/or employing any number and combination of computing devices and networks utilizing various communication technologies, as described herein. The computer system 500 can be easily scalable, extensible, and modular, with the ability to change to different services or reconfigure some features independently of others. The computer system 500 may be, for example, a server, desktop computer, laptop computer, tablet computer, or smartphone. In some examples, computer system 500 may be a cloud computing node. Computer system 500 may be described in the general context of computer system executable instructions, such as program modules, being executed by a computer system. Generally, program modules may include routines, programs, objects, components, logic, data structures, and so on that perform particular tasks or implement particular abstract data types. Computer system 500 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, the computer system 500 has one or more central processing units (CPU(s)) 501*a*, 501*b*, 501*c*, etc. (collectively or generically referred to as processor(s) 501). The processors 501 can be a single-core processor, multi-core processor, computing cluster, or any number of other configurations. The processors 501, also referred to as processing circuits, are coupled via a system bus 502 to a system memory 503 and various other components. The system memory 503 can include a read only memory (ROM) 504 and a random access memory (RAM) 505. The ROM 504 is coupled to the system bus 502 and may include a basic input/output system (BIOS), which controls certain basic functions of the computer system 500. The RAM is read-write memory coupled to the system bus 502 for use by the processors 501. The system memory 503 provides temporary memory space for operations of said instructions during operation. The system memory 503 can include random access memory (RAM), read only memory, flash memory, or any other suitable memory systems.

The computer system 500 comprises an input/output (I/O) adapter 506 and a communications adapter 507 coupled to the system bus 502. The I/O adapter 506 may be a small computer system interface (SCSI) adapter that communicates with a hard disk 508 and/or any other similar component. The I/O adapter 506 and the hard disk 508 are collectively referred to herein as a mass storage 510.

Software 511 for execution on the computer system 500 may be stored in the mass storage 510. The mass storage 510 is an example of a tangible storage medium readable by the processors 501, where the software 511 is stored as instructions for execution by the processors 501 to cause the computer system 500 to operate, such as is described herein below with respect to the various Figures. Examples of computer program product and the execution of such instruction is discussed herein in more detail. The communications adapter 507 interconnects the system bus 502 with a network 512, which may be an outside network, enabling the computer system 500 to communicate with other such systems. In one embodiment, a portion of the system memory 503 and the mass storage 510 collectively store an operating system, which may be any appropriate operating system, such as the z/OS or AIX operating system from IBM Corporation, to coordinate the functions of the various components shown in FIG. 5.

Additional input/output devices are shown as connected to the system bus 502 via a display adapter 515 and an interface adapter 516 and. In one embodiment, the adapters 506, 507, 515, and 516 may be connected to one or more I/O buses that are connected to the system bus 502 via an intermediate bus bridge (not shown). A display 519 (e.g., a screen or a display monitor) is connected to the system bus 502 by a display adapter 515, which may include a graphics controller to improve the performance of graphics intensive applications and a video controller. A keyboard 521, a mouse 522, a speaker 523, etc. can be interconnected to the system bus 502 via the interface adapter 516, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 5, the computer system 500 includes processing capability in the form of the processors 501, and, storage capability including the system memory 503 and the mass storage 510, input means such as the keyboard 521 and the mouse 522, and output capability including the speaker 523 and the display 519.

In some embodiments, the communications adapter 507 can transmit data using any suitable interface or protocol, such as the internet small computer system interface, among others. The network 512 may be a cellular network, a radio network, a wide area network (WAN), a local area network (LAN), or the Internet, among others. An external computing device may connect to the computer system 500 through the network 512. In some examples, an external computing device may be an external webserver or a cloud computing node.

It is to be understood that the block diagram of FIG. 5 is not intended to indicate that the computer system 500 is to include all of the components shown in FIG. 5. Rather, the computer system 500 can include any appropriate fewer or additional components not illustrated in FIG. 5 (e.g., additional memory components, embedded controllers, modules, additional network interfaces, etc.). Further, the embodiments described herein with respect to computer system 500 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted, or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
    adding, by a processor, a first plurality of randomly generated compression algorithms to a first set of compression algorithms, wherein the first plurality of randomly generated compression algorithms is generated based on a library of reversible matrix operations;
    determining, by the processor, a respective mutated version of each of the first plurality of randomly generated compression algorithms by substituting one or more operations in each of the first plurality of randomly generated compression algorithms based on the library of reversible matrix operations;
    adding, by the processor, the determined mutated versions to the first set of compression algorithms;
    evaluating and ranking, by the processor, the first set of compression algorithms based on respective achieved degrees of compression for a data type; and
    identifying, by the processor, a winning compression algorithm based on the evaluation and ranking of the first set of compression algorithms, wherein the winning compression algorithm is used to compress data files corresponding to the data type.

2. The method of claim 1, wherein adding the first plurality of randomly generated compression algorithms to the first set of compression algorithms comprises:
    generating, by a processor, an initial set of compression algorithms based on the library of reversible matrix operations;
    evaluating and ranking the initial set of compression algorithms based on respective achieved degrees of compression; and
    determining a top tier of the ranked initial set of compression algorithms, wherein the determined top tier of the ranked initial set of compression algorithms is the first plurality of randomly generated compression algorithms.

3. The method of claim 1, further comprising adding a second plurality of randomly generated compression algorithms to the first set of compression algorithms before evaluating and ranking the first set of compression algorithms.

4. The method of claim 1, further comprising:
    determining a top tier of the ranked first set of compression algorithms;
    adding the top tier of the ranked first set of compression algorithms to a second set of compression algorithms;
    determining a respective mutated version of each of the top tier of the ranked first set of compression algorithms;

adding the determined mutated versions to the second set of compression algorithms; and
evaluating and ranking the second set of compression algorithms based on respective achieved degrees of compression.

5. The method of claim 4, wherein evaluating and ranking the first set of compression algorithms based on respective achieved degrees of compression is performed based on first input data corresponding to the data type; and
wherein evaluating and ranking the second set of compression algorithms based on respective achieved degrees of compression is performed based on second input data corresponding to the data type.

6. The method of claim 5, further comprising determining the winning compression algorithm and corresponding winning decompression algorithm for the data type based on the ranked second set of compression algorithms.

7. The method of claim 6, further comprising:
receiving a file corresponding to the data type by a compression application, the compression application comprising a plurality of compression algorithms including the winning compression algorithm;
compressing the file by the winning compression algorithm based on the data type;
inserting an algorithm identifier corresponding to the winning compression algorithm into metadata of the compressed file;
receiving the compressed file by a decompression application, the decompression application comprising a plurality of decompression algorithms including the winning decompression algorithm; and
decompressing the compressed file by the winning decompression algorithm based on the algorithm identifier.

8. A system comprising:
a memory having computer readable instructions; and
one or more processors for executing the computer readable instructions, the computer readable instructions controlling the one or more processors to perform operations comprising:
adding a first plurality of randomly generated compression algorithms to a first set of compression algorithms, wherein the first plurality of randomly generated compression algorithms is generated based on a library of reversible matrix operations;
determining a respective mutated version of each of the first plurality of randomly generated compression algorithms by substituting one or more operations in each of the first plurality of randomly generated compression algorithms based on the library of reversible matrix operations;
adding the determined mutated versions to the first set of compression algorithms;
evaluating and ranking the first set of compression algorithms based on respective achieved degrees of compression for a data type; and
identifying a winning compression algorithm based on the evaluation and ranking of the first set of compression algorithms, wherein the winning compression algorithm is used to compress data files corresponding to the data type.

9. The system of claim 8, wherein adding the first plurality of randomly generated compression algorithms to the first set of compression algorithms comprises:
generating an initial set of compression algorithms based on the library of reversible matrix operations;
evaluating and ranking the initial set of compression algorithms based on respective achieved degrees of compression; and
determining a top tier of the ranked initial set of compression algorithms, wherein the determined top tier of the ranked initial set of compression algorithms is the first plurality of randomly generated compression algorithms.

10. The system of claim 8, wherein the operations further comprise adding a second plurality of randomly generated compression algorithms to the first set of compression algorithms before evaluating and ranking the first set of compression algorithms.

11. The system of claim 8, wherein the operations further comprise:
determining a top tier of the ranked first set of compression algorithms;
adding the top tier of the ranked first set of compression algorithms to a second set of compression algorithms;
determining a respective mutated version of each of the top tier of the ranked first set of compression algorithms;
adding the determined mutated versions to the second set of compression algorithms; and
evaluating and ranking the second set of compression algorithms based on respective achieved degrees of compression.

12. The system of claim 11, wherein evaluating and ranking the first set of compression algorithms based on respective achieved degrees of compression is performed based on first input data corresponding to the data type; and
wherein evaluating and ranking the second set of compression algorithms based on respective achieved degrees of compression is performed based on second input data corresponding to the data type.

13. The system of claim 12, wherein the operations further comprise determining the winning compression algorithm and corresponding winning decompression algorithm for the data type based on the ranked second set of compression algorithms.

14. The system of claim 13, wherein the operations further comprise:
receiving a file corresponding to the data type by a compression application, the compression application comprising a plurality of compression algorithms including the winning compression algorithm;
compressing the file by the winning compression algorithm based on the data type;
inserting an algorithm identifier corresponding to the winning compression algorithm into metadata of the compressed file;
receiving the compressed file by a decompression application, the decompression application comprising a plurality of decompression algorithms including the winning decompression algorithm; and
decompressing the compressed file by the winning decompression algorithm based on the algorithm identifier.

15. A computer program product comprising a computer readable storage medium having program instructions embodied therewith, the program instructions executable by one or more processors to cause the one or more processors to perform operations comprising:
adding a first plurality of randomly generated compression algorithms to a first set of compression algorithms, wherein the first plurality of randomly generated compression algorithms is generated based on a library of reversible matrix operations;

determining a respective mutated version of each of the first plurality of randomly generated compression algorithms by substituting one or more operations in each of the first plurality of randomly generated compression algorithms based on the library of reversible matrix operations;

adding the determined mutated versions to the first set of compression algorithms;

evaluating and ranking the first set of compression algorithms based on respective achieved degrees of compression for a data type; and identifying a winning compression algorithm based on the evaluation and ranking of the first set of compression algorithms, wherein the winning compression algorithm is used to compress data files corresponding to the data type.

16. The computer program product of claim 15, wherein adding the first plurality of randomly generated compression algorithms to the first set of compression algorithms comprises:

generating an initial set of compression algorithms based on the library of reversible matrix operations;

evaluating and ranking the initial set of compression algorithms based on respective achieved degrees of compression; and determining a top tier of the ranked initial set of compression algorithms, wherein the determined top tier of the ranked initial set of compression algorithms is the first plurality of randomly generated compression algorithms.

17. The computer program product of claim 15, wherein the operations further comprise adding a second plurality of randomly generated compression algorithms to the first set of compression algorithms before evaluating and ranking the first set of compression algorithms.

18. The computer program product of claim 15, wherein the operations further comprise:

determining a top tier of the ranked first set of compression algorithms;

adding the top tier of the ranked first set of compression algorithms to a second set of compression algorithms;

determining a respective mutated version of each of the top tier of the ranked first set of compression algorithms;

adding the determined mutated versions to the second set of compression algorithms; and evaluating and ranking the second set of compression algorithms based on respective achieved degrees of compression.

19. The computer program product of claim 18, wherein evaluating and ranking the first set of compression algorithms based on respective achieved degrees of compression is performed based on first input data corresponding to the data type; and wherein evaluating and ranking the second set of compression algorithms based on respective achieved degrees of compression is performed based on second input data corresponding to the data type.

20. The computer program product of claim 19, wherein the operations further comprise determining the winning compression algorithm and corresponding winning decompression algorithm for the data type based on the ranked second set of compression algorithms.

* * * * *